(12) United States Patent
Lutze et al.

(10) Patent No.: US 8,353,898 B2
(45) Date of Patent: Jan. 15, 2013

(54) SURGICAL INSTRUMENT

(75) Inventors: Theodor Lutze, Balgheim (DE); Olaf Hegemann, Tuebingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 13/304,803

(22) Filed: Nov. 28, 2011

(65) Prior Publication Data

US 2012/0123396 A1 May 17, 2012

Related U.S. Application Data

(63) Continuation of application No. PCT/EP2010/055279, filed on Apr. 21, 2010.

(30) Foreign Application Priority Data

May 29, 2009 (DE) .......................... 10 2009 024 233
Sep. 14, 2009 (DE) .......................... 10 2009 042 150

(51) Int. Cl.
*A61B 19/00* (2006.01)
(52) U.S. Cl. ........................................... 606/1; 606/130
(58) Field of Classification Search ........................ None
See application file for complete search history.

(56) References Cited

U.S. PATENT DOCUMENTS

| | | | |
|---|---|---|---|
| 338,310 A | 3/1886 | Smith | |
| 2,515,365 A | 7/1950 | Zublin | |
| 2,694,549 A | 11/1954 | James | |
| 2,712,436 A | 7/1955 | McCune et al. | |
| 2,739,089 A | 3/1956 | Hageltorn | |
| 3,096,962 A | 7/1963 | Meijs | |
| 3,190,286 A | 6/1965 | Stokes | |
| 3,625,200 A | 12/1971 | Muller | |
| 3,674,014 A | 7/1972 | Tillander | |
| 4,328,839 A | 5/1982 | Lyons et al. | |
| 4,600,037 A | 7/1986 | Hatten | |
| 4,706,659 A | 11/1987 | Matthews et al. | |
| 4,790,294 A | 12/1988 | Allred, III et al. | |
| 4,955,384 A | 9/1990 | Taylor et al. | |
| 5,152,744 A | 10/1992 | Krause et al. | |
| 5,179,934 A | 1/1993 | Nagayoshi et al. | |
| 5,437,630 A * | 8/1995 | Daniel et al. ..................... | 604/22 |
| 5,695,513 A | 12/1997 | Johnson et al. | |
| 5,755,731 A | 5/1998 | Grinberg | |
| 5,807,241 A | 9/1998 | Heimberger | |
| 5,833,692 A * | 11/1998 | Cesarini et al. ................. | 606/79 |

(Continued)

FOREIGN PATENT DOCUMENTS

CH 119033 4/1927

(Continued)

*Primary Examiner* — Henry M Johnson, III
(74) *Attorney, Agent, or Firm* — Lipsitz & McAllister, LLC

(57) ABSTRACT

A surgical instrument is provided, comprising proximal and distal end sections each comprising an area of articulation, as well as a flexurally rigid central section arranged therebetween. The proximal end section can be connected to an actuating device. A tool which can be driven by means of a drive element can be connected to the distal end section. To provide greater flexibility and a greater working area, the instrument further comprises outer and inner hollow cylindrical shafts and a control element which is arranged between the shafts. Two or more longitudinal elements extend at least substantially from the proximal to the distal area of articulation of the instrument and transfer traction and/or pressure forces. The longitudinal elements are arranged at essentially regular angular distances in a circumferential direction of the instrument and are connected to one another in the circumferential direction at their proximal and distal ends.

30 Claims, 6 Drawing Sheets

U.S. PATENT DOCUMENTS

| | | | | |
|---|---|---|---|---|
| 5,921,956 | A * | 7/1999 | Grinberg et al. | 604/95.01 |
| 6,053,922 | A | 4/2000 | Krause et al. | |
| 6,132,448 | A * | 10/2000 | Perez et al. | 606/180 |
| 6,352,531 | B1 * | 3/2002 | O'Connor et al. | 606/15 |
| 6,409,728 | B1 * | 6/2002 | Ehr et al. | 606/51 |
| 6,447,518 | B1 | 9/2002 | Krause et al. | |
| 6,817,974 | B2 | 11/2004 | Cooper et al. | |
| 6,921,397 | B2 | 7/2005 | Corcoran et al. | |
| 7,090,683 | B2 * | 8/2006 | Brock et al. | 606/130 |
| 7,105,003 | B2 | 9/2006 | Hiltebrandt | |
| 7,608,083 | B2 | 10/2009 | Lee et al. | |
| 2002/0032368 | A1 | 3/2002 | Takase | |
| 2004/0102772 | A1 * | 5/2004 | Baxter et al. | 606/45 |
| 2005/0096694 | A1 | 5/2005 | Lee | |
| 2005/0216018 | A1 | 9/2005 | Sennett | |
| 2005/0216033 | A1 | 9/2005 | Lee et al. | |
| 2006/0178556 | A1 | 8/2006 | Hasser et al. | |
| 2007/0010823 | A1 | 1/2007 | Kucklick | |
| 2007/0118135 | A1 * | 5/2007 | Mansmann | 606/80 |
| 2007/0219539 | A1 | 9/2007 | Efinger et al. | |
| 2007/0282371 | A1 | 12/2007 | Lee et al. | |
| 2008/0077146 | A1 * | 3/2008 | Pernsteiner et al. | 606/79 |
| 2008/0234545 | A1 | 9/2008 | Breedveld et al. | |
| 2010/0151161 | A1 | 6/2010 | Da Rolo | |
| 2010/0286694 | A1 * | 11/2010 | Rio et al. | 606/80 |
| 2011/0004157 | A1 | 1/2011 | Dewaele et al. | |
| 2011/0034764 | A1 * | 2/2011 | Verbeek | 600/101 |

FOREIGN PATENT DOCUMENTS

| | | |
|---|---|---|
| DE | 40 02 449 | 8/1990 |
| DE | 695 17 463 | 3/2001 |
| DE | 10 2004 046 539 | 4/2006 |
| DE | 20 2009 007 979 | 9/2009 |
| DE | 20 2009 012 795 | 1/2010 |
| EP | 0 445 918 | 9/1991 |
| EP | 0 626 604 | 11/1994 |
| EP | 0 677 276 | 6/2000 |
| EP | 0 986 989 | 1/2002 |
| EP | 1 243 283 | 9/2002 |
| EP | 0 840 572 | 10/2004 |
| EP | 0 764 423 | 3/2010 |
| WO | 93/13713 | 7/1993 |
| WO | 99/15090 | 4/1999 |
| WO | 2005/067785 | 7/2005 |
| WO | 2006/113216 | 10/2006 |
| WO | 2007/039875 | 4/2007 |
| WO | 2007/146842 | 12/2007 |
| WO | 2009/088430 | 7/2009 |
| WO | 2009/098244 | 8/2009 |
| WO | 2009/112060 | 9/2009 |
| WO | WO 2011/162853 | 12/2011 |

* cited by examiner

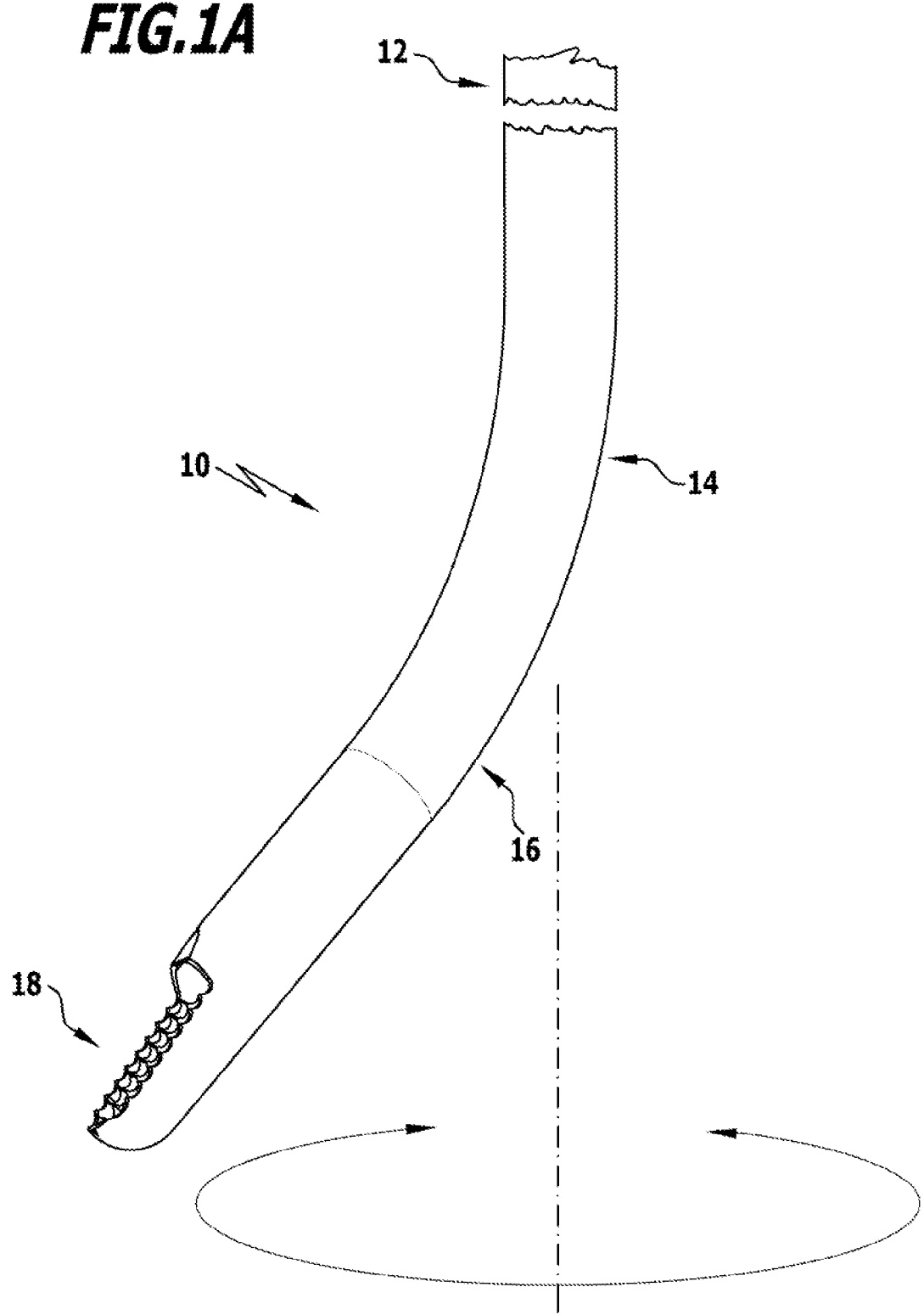

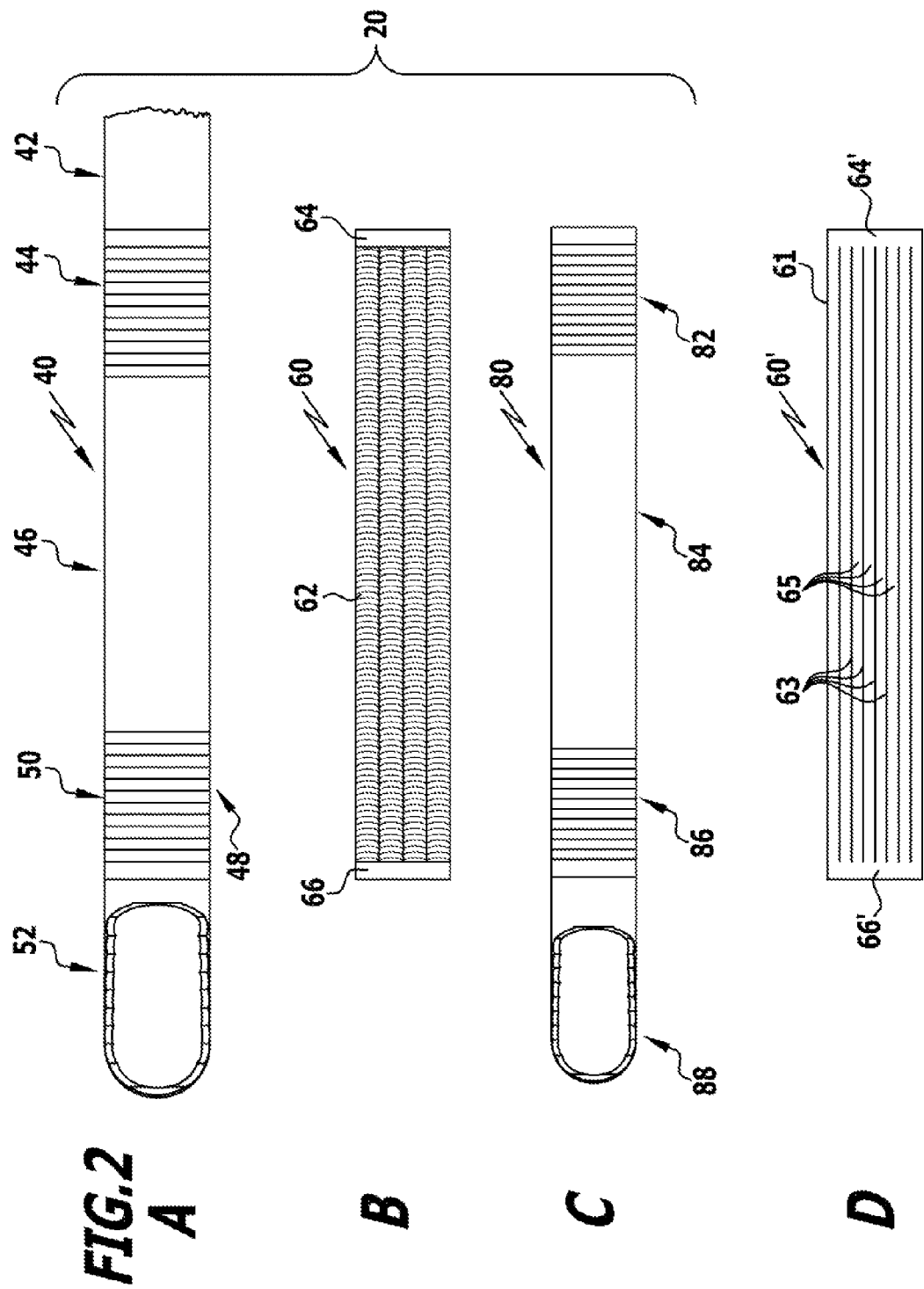

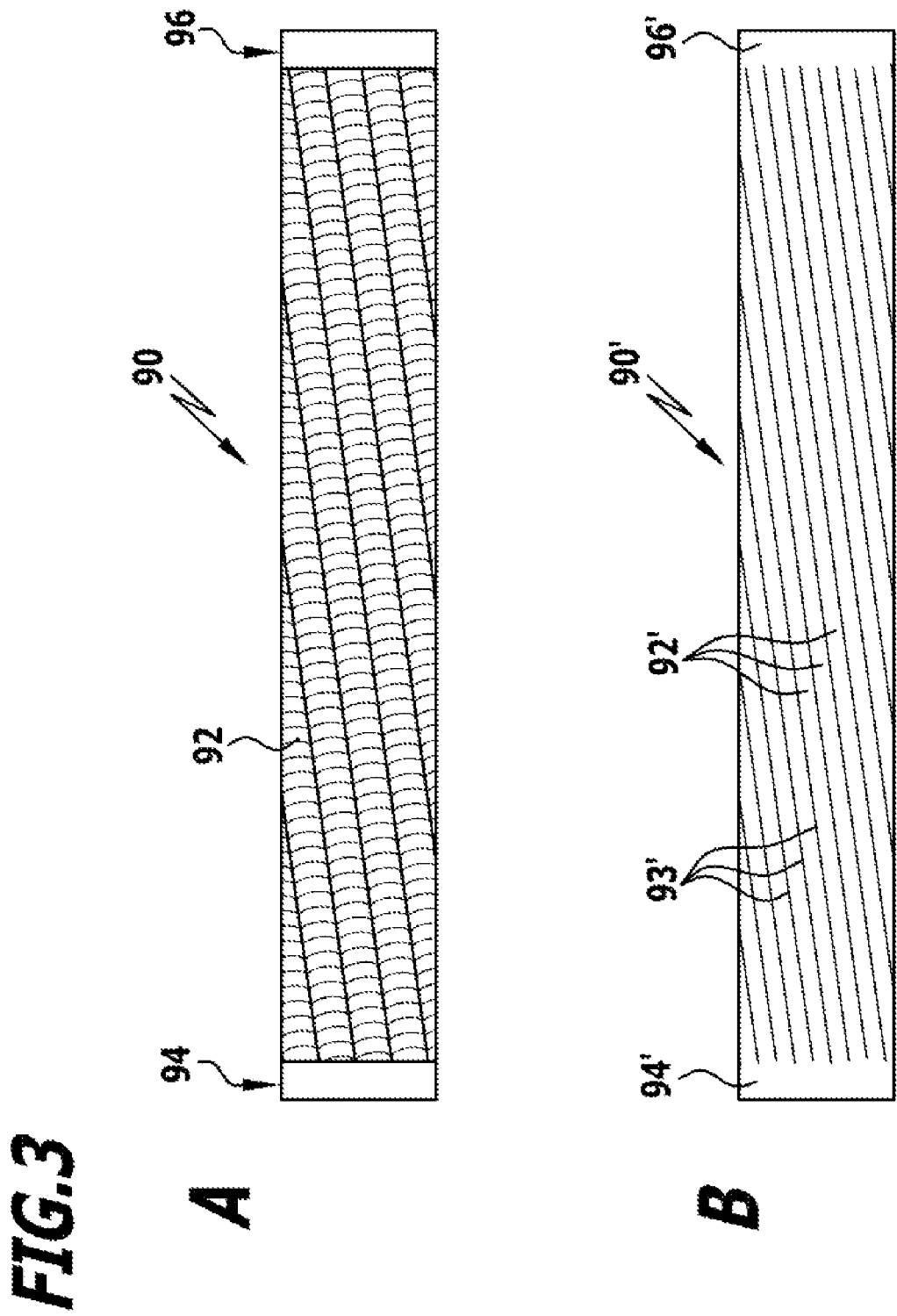

SURGICAL INSTRUMENT

This application is a continuation of international application number PCT/EP2010/055279 filed on Apr. 21, 2010 and claims the benefit of German application number 10 2009 024 233.3 filed on May 29, 2009 and German application number 10 2009 042 150.5 filed Sep. 14, 2009.

The present disclosure relates to the subject matter disclosed in international application number PCT/EP2010/055279 of Apr. 21, 2010 and German applications number 10 2009 024 233.3 of May 29, 2009 and number 10 2009 042 150.5 of Sep. 14, 2009, which are incorporated herein by reference in their entirety and for all purposes.

BACKGROUND OF THE INVENTION

The invention relates to a surgical instrument, in particular for use in combination with a trocar or the like, comprising a proximal and a distal end section each comprising an area of articulation as well as a flexurally rigid central section arranged therebetween.

The proximal end section can be connected to an actuating device, also, in particular, to a motor drive device, and a cutting, abrasive or milling tool which can be driven by means of a drive element is connected to the distal end section.

It is known to design such surgical instruments so as to be slightly angled in the distal end section in order to increase their working area, for example through 20° in relation to the longitudinal direction of the instrument, as is known from EP 0 677 276 B1 or also DE 10 2004 046 539 A1.

Despite the angling of the distal end section, the working area on the patient which can, as a result, be reached is still comparatively restricted and, in particular, pieces of tissue which are difficult to reach still require, in some cases, the renewed placement of the trocar which is, in general, undesired.

The object of the present invention is to develop the surgical instrument specified at the outset further such that its use is more flexible and it has a greater working area.

SUMMARY OF THE INVENTION

This object is accomplished in accordance with the invention, with the surgical instrument described at the outset, in that the instrument comprises an outer hollow cylindrical shaft, an inner hollow cylindrical shaft as well as a control element which is arranged between these shafts and has two or more longitudinal elements which extend at least substantially from the proximal to the distal area of articulation of the instrument and transfer traction and/or pressure forces. The longitudinal elements are, in this respect, arranged at essentially regular angular distances in circumferential direction of the instrument and are connected to one another in circumferential direction at their proximal and distal ends.

On account of this configuration of the surgical instrument, pivoting movements may be carried out at the proximal end section, to which pivoting movements at the distal end section then correspond.

In comparison with the instruments of the state of the art, instead of the straight-lined (linear) or stationarily curved configuration a configuration is possible which is straight-lined or adjustably curved as required and this configuration can also be varied during surgical use during an operation within predetermined limits.

The coupling of the pivoting movement at the proximal and distal end sections is brought about by the control element and its force transferring longitudinal elements.

If two force transferring longitudinal elements are used, the pivoting movement is restricted to one plane. If several, in particular four or more, for example eight force transferring longitudinal elements are used, it is possible to pivot the surgical instrument in two planes at right angles to one another or, however, in particular in the case where eight control elements or more are used, to pivot them in planes which can be selected practically arbitrarily.

The pivoting movements are not restricted to angles of approximately 20° but rather pivoting movements up to and far beyond 90° can certainly be achieved.

In one preferred embodiment of the invention, the instrument has a control element which comprises a hollow cylindrical component, the cylinder wall of which is subdivided into two or more wall segments, which form the force transferring longitudinal elements, at least in the region of a section between the proximal and distal ends.

In this respect, the two or more wall segments can be connected fixedly to one another via an annular collar at the distal end of the hollow cylindrical component.

In addition, the two or more wall segments can be connected fixedly to one another in the region of the proximal end of the hollow cylindrical component.

It is particularly preferred to have the hollow cylindrical component designed in one piece. In this case, the handling during assembly of the instrument is particularly simple. Moreover, the one-piece component may be produced with particular precision with respect to the mutual alignment of the wall segments.

Instruments of this configuration have, in particular, a hollow cylindrical component which is manufactured from a single small tube, wherein the subdivision of the cylinder wall into wall segments is preferably brought about by means of laser beam cutting.

Steel alloys or nitinol lend themselves, in particular, as material for the production of the control element, in particular of the hollow cylindrical component.

In one particularly preferred embodiment of the invention, the inner shaft of the instrument is designed as drive element and so a lumen which is as large as possible remains free, for example, for removing pieces of tissue of the patient being treated which have been cut away with the tool.

The drive element has two flexible sections which are arranged in the proximal and distal areas of articulation, respectively, within the outer shaft in the assembled state of the instrument. As a result, it is possible for the typically rotational drive movement to be transferred to the tool connected to the distal end section even in the angled state.

In order to achieve as effective a transfer as possible of the rotational momentum, the drive element is designed to be essentially torsionally rigid.

The outer shaft is also preferably designed to be torsionally rigid in order to absorb the reaction forces occurring during operation of the tool and to avoid any deformation of the instrument. A deformation of the instrument would result in the instrument being moved away from its respective application site, an effect which could lead to considerable complications in the case of operations which have to be carried out extremely precisely.

In a further embodiment of the present invention, the areas of articulation are designed to be elastic, preferably flexurally elastic, so that the surgical instrument will be returned to the straight shape when the forces which cause a pivoting movement at the proximal end cease.

The force transferring longitudinal elements are, in one variation of the present invention, arranged so as to be laterally spaced relative to one another and so they do not rub against one another during the pivoting movement and thus the pivoting movement can be carried out with a minimal expenditure of force.

Alternatively, a spacer element may be arranged between the respective, laterally spaced longitudinal elements so that the position in circumferential direction of the longitudinal elements remains essentially unchanged even when greater forces are introduced for carrying out the pivoting movement.

Alternatively, it may be provided for the force transferring longitudinal elements to be arranged along the longitudinal direction at least partially in direct contact with one another. In this case, as well, it is ensured that the longitudinal elements remain in their positions when seen in the circumferential direction, even when force is introduced, and, therefore, an exact control of the pivoting movement of the distal end can be achieved.

It is even more preferred when the force transferring longitudinal elements are guided in a radial direction by the outer and the inner shaft which leads to a further improvement in the accuracy of the pivoting movement carried out at the distal end.

In accordance with a further embodiment of the present invention, it may be provided, in the case of the control element to be used in accordance with the invention, for the distal ends of the longitudinal elements to be secured in a circumferential direction in angular positions which differ from the angular positions, in which the respectively associated proximal ends are secured.

This allows pivoting movements of the distal end to be carried out in a different plane to that, in which the pivoting movement of the proximal end is carried out.

The angular difference, in which the angular positions of the distal and the proximal ends of a longitudinal element are secured, can range from approximately 10° to approximately 350°. Differences in the angular positions at the proximal and distal ends in the range of approximately 45° to approximately 315° are of interest, in particular, even more preferred in the range of approximately 150° to approximately 210°.

In order to achieve this, the force transferring longitudinal elements are preferably arranged in a helical shape at least in sections.

With regard to the typical length of a surgical instrument and the length of the longitudinal element resulting therefrom and the, at the same time, relatively small diameter, angular positions of the longitudinal elements, which deviate from the axial direction of the instrument to a very slight extent, result on their helically shaped path. This means that a reliable handling of the instrument is ensured even with a very large angular offset of, for example, 180° and, in particular, the pivoting movement of the distal end can also be carried out in an angularly exact and predictable manner.

In a further embodiment of the invention, it may be provided for the force transferring longitudinal elements to be arranged in the region of the proximal and/or distal end sections with an essentially parallel alignment in relation to the longitudinal axis of the instrument.

Alternatively, one or more sections can also be arranged parallel to the longitudinal direction of the instrument.

In this case, as well, with respect to the typical length of the control element required of at least more than 10 cm and with a typical diameter of the instrument of a few millimeters, an extremely high pitch of the helical shape results or, expressed differently, a very small deviation from the parallelism in relation to the longitudinal direction of the instrument which is a few degrees of angle up to a fraction of a degree of angle.

In accordance with one variation of the instrument according to the invention, the force transferring longitudinal elements are designed as cables or wires.

In another variation, the force transferring longitudinal elements have a banana-shaped cross section.

As explained above, the force transferring longitudinal elements of a particularly preferred embodiment are formed from a hollow cylindrical component, with which, for example by means of laser beam cutting, the cylinder wall is slit over the greatest part, in particular more or less over the entire length in axial direction for the purpose of forming the force transferring longitudinal elements. The longitudinal elements are formed, in this respect, by cylinder wall segments which have an arc shape in cross section.

The wall segments preferably have in cross section an arc shape which corresponds to an arc angle of approximately 20° or more, in particular 30° or more.

The number of wall segments is preferably in the range of 4 to 16, even more preferred in the range of 6 to 12.

The distance of the wall segments from one another in circumferential direction (corresponds to the width of the slit) is, measured in degrees of angle, preferably approximately 2° to 15°, even more preferred approximately 4° to approximately 8°.

The width of the slit, which results during the laser beam cutting, can be increased as required and so the remaining strip-like wall segments can be moved relative to one another without contact. On account of the circular segment-like cross sections of the longitudinal elements, the contact-less state of the longitudinal elements is also retained in the case of the traction or pressure tensioning even in the areas of articulation; this applies, in particular, for a guidance of the longitudinal elements in a radial direction between an inner and an outer shaft.

The two end areas of the hollow cylindrical element remain without any slit and so the longitudinal elements remain connected to one another via annular collars.

The proximal and distal areas of articulation of the instrument can be realized in different ways.

If the inner shaft is used as drive element, it has from the start, in the region of the areas of articulation, flexible sections which can be adequate for realizing the proximal and distal areas of articulation. This means that the outer shaft must be correspondingly flexible in order to likewise follow the pivoting movements initiated by the control element.

Alternatively, the inner and the outer shafts can both have a proximal and a distal section of articulation in the region of the proximal and distal areas of articulation, wherein when the inner shaft is used as drive element its flexible sections correspond to the proximal and distal section of articulation, respectively.

The areas of articulation of the outer and/or inner shaft preferably have several slits which extend in circumferential direction and are separated from one another in circumferential direction or rather axial direction by wall areas.

A respective wall section preferably has in circumferential direction two or more, in particular three or more, slits arranged one behind the other. The slits are preferably arranged in circumferential direction at equal distances from one another.

In an axial direction, the areas of articulation of preferred instruments have three or more slits arranged next to one another, wherein the slits arranged next to one another are preferably arranged so as to be offset relative to one another in circumferential direction. The distances, at which the slits are arranged in an axial direction so as to be spaced from one another, may be equal or vary, wherein the articulation properties, in particular the bending radius, can be influenced hereby.

Typically, it is provided for the slits to be slits penetrating the cylinder wall completely. Good bending properties may, however, also be achieved when the slits do not penetrate the wall of the shaft completely but rather end, in particular, before reaching the inner circumference. As a result, the wall of the shaft remains complete as a whole which can be desirable in some applications, in particular in the case of the outer shaft.

One preferred geometry of the slit is present when the wall surfaces delimiting the slits are arranged at an acute angle relative to the radial direction. In this respect, wall surfaces of the same slit which are located opposite one another will preferably be arranged in mirror image so that a greater slit width results at the outer circumference of a shaft than adjacent to the inner circumference.

Slits which are spaced from one another in axial direction will preferably be arranged in circumferential direction so as to overlap but be offset relative to one another so that a regular arrangement of the slits results.

The wall surfaces of the slits can be inclined relative to the axial direction at an angle which deviates from 90° so that the width of the slits at the outer circumference is greater than at the inner circumference of the outer shaft. As a result, sufficiently large pivoting angles may be realized even with small slit widths without the number of slits needing to be increased or the region of articulation needing to extend over a greater axial length.

Whereas, in many cases, the proximal and the distal areas of articulation are designed the same and, in particular, have an equal extension in longitudinal direction of the instrument, this is not absolutely necessary.

It may, in particular, be provided for the proximal and the distal areas of articulation to be of a different design, in particular also be designed with different lengths. As a result, it is possible, for example, for a corresponding pivoting movement of the proximal area of articulation to result in a smaller or intensified pivoting movement at the distal end section of the instrument.

It may be provided, in particular, for the pivoting movement of the proximal and/or distal areas of articulation to be adjustable. This can be brought about, for example, in that the extension of the proximal and/or the distal area of articulation will be varied and, therefore, the pivoting behavior of the two areas of articulation will be altered relative to one another.

It may be provided, in particular, for the instrument to comprise a holding device, with which parts of one of the areas of articulation can be fixed in position in a flexurally rigid manner with respect to the central section or a functional unit adjoining the proximal or distal end section of the instrument.

In one variation of the instrument according to the invention, the holding device can comprise a flexurally rigid sleeve which is displaceable parallel to the longitudinal axis of the flexurally rigid central section. Depending on the position of the sleeve in longitudinal direction relative to the central section, the proximal and/or distal end section and the area of articulation provided there can be influenced in their length and, as a result, can likewise be influenced in their pivoting behavior.

In this respect, the flexurally rigid sleeve will preferably be arranged on the outer circumference of the flexurally rigid shaft so that not only does the lumen of the control device remain unaffected but also the position of the sleeve is easy to alter and can also, in particular, be easily secured.

In accordance with another variation, the holding device can comprise a supporting holding element on the functional unit which is coupled to the proximal end of the control device. In this way, the area of articulation can be influenced in its pivoting behavior from the proximal end side.

In accordance with a further variation of the instrument according to the invention, the holding device can be positioned and, in particular, also secured in a predetermined position. As a result, it is possible to adjust in advance or readjust the pivoting behavior of distal and proximal end sections relative to one another in a manner which can be repeated and exactly predetermined.

These and other advantages of the invention will be explained in greater detail in the following on the basis of the drawings.

BRIEF DESCRIPTION OF THE DRAWINGS

FIG. 1A shows a surgical instrument in the form of a shaver in accordance with the state of the art;

FIGS. 3A and B show two variations of an alternative embodiment of a control element for the surgical instrument according to the invention of FIG. 1B.

DETAILED DESCRIPTION OF THE INVENTION

Figure 1B:
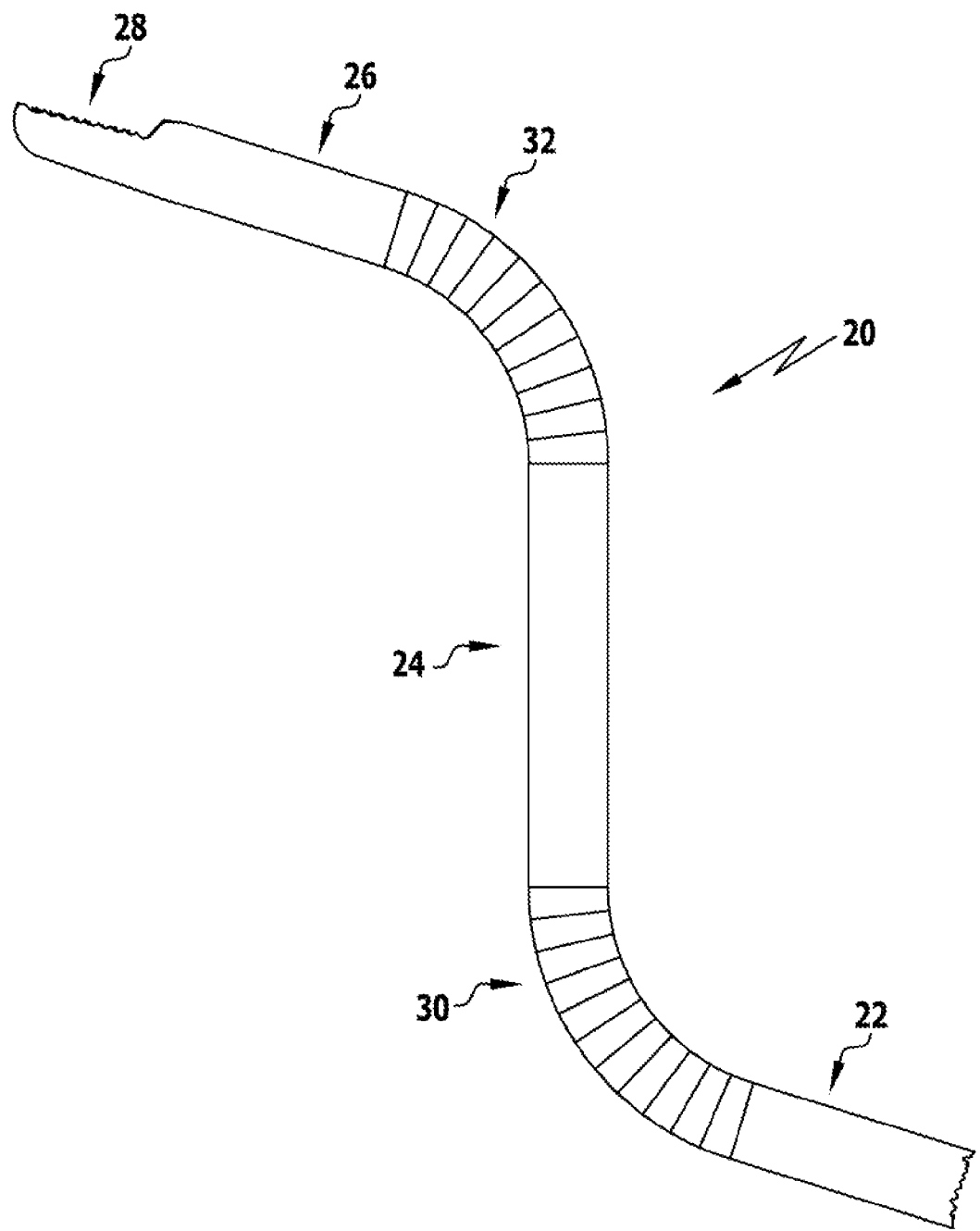
FIG. 1B shows a surgical instrument in the form of a shaver in accordance with the present invention.

FIG. 1A shows a conventional surgical instrument in the form of a shaver 10 with a proximal end 12, a straight, flexurally rigid shaft 14 as well as a slightly angled distal end section 16, with which a tool, for example a cutting, abrasive or milling tool, is connected, in particular integrally formed.

Reference may be made, for example, to DE 10 2004 046 539 A1 regarding the details of such an instrument.

Drilling tools can also be used with the instrument according to the invention, wherein the distal end of the instrument is then not closed and instead of the side opening an opening in axial direction is present for passage of the drilling tool.

The angle, at which the distal end section 16 deviates from the longitudinal direction of the instrument 10, will be predetermined during production and remains unaltered.

The instrument can cover a limited working area, which is already clearly increased in comparison with the straight-line configuration of the instrument which is likewise already known, as a result of rotation about the longitudinal axis of the shaft 14 which is typically guided in a trocar.

In accordance with the present invention, a surgical instrument with a proximal and a distal area of articulation is provided, which is shown with the example of the shaver 20 in FIG. 1B and intended to be discussed in the following.

The shaver 20 according to the invention has a shaft which is divided into a proximal end section 22, a flexurally rigid central section 24 as well as a distal end section 26.

A tool 28 is connected to or integrally formed on the distal end section 26 and this can correspond in its design to that described, for example, in DE 10 2004 046 539 A1.

The proximal and the distal end sections 22, 26 of the instrument 20 each comprise an area of articulation 30, 32 which allows a pivoting movement of the proximal end section 22 which may be converted into a pivoting movement of the distal end section 26 at the section of articulation 32 on account of a control element of the instrument 20. As a result, the shaver 20 of FIG. 1B can be operated not only in a straight-line alignment, with a slight angling of the distal end section 26 as well as with a more or less right-angled bending of the end section 26 which provides the instrument with a considerably larger working area and also makes operating positions which are difficult to reach accessible.

It may be provided, in particular, for the pivoting movement of the proximal and/or distal areas of articulation 30, 32 to be adjustable. This can be brought about, for example, in that the extension of the proximal and/or the distal areas of articulation 30, 32 will be varied and, therefore, the pivoting behavior of the two areas of articulation 30, 32 will be altered relative to one another. For example, as shown in FIG. 1C, the instrument may comprise a holding device 34, with which parts of one of the areas of articulation 30, 32 can be fixed in position in a flexurally rigid manner with respect to the central section 24 or a functional unit adjoining the proximal or distal end section 22, 26 of the instrument.

Figure 1C:
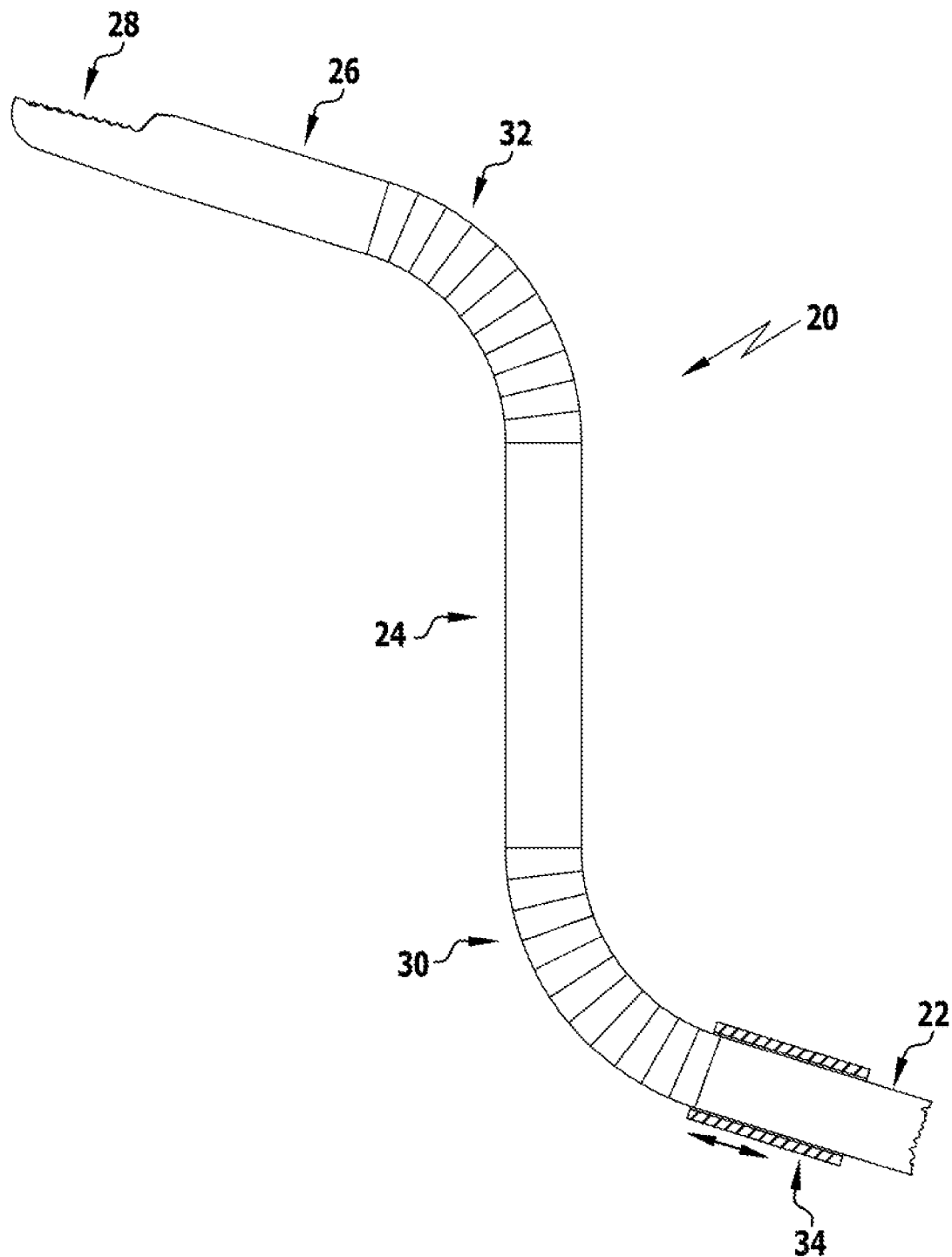
FIG. 1C shows an embodiment of a surgical instrument with a holding device for fixing an area of articulation in position in accordance with the present invention.

In the example embodiment of FIG. 1C, the holding device 34 comprises a flexurally rigid sleeve which is displaceable parallel to the longitudinal axis of the flexurally rigid central section 24. Depending on the position of the sleeve 34 in longitudinal direction relative to the central section 24, the corresponding area of articulation 30 or 32 can be influenced in its length and, as a result, the extension of the areas of articulation 30, 32 are both influenced and adjusted in their pivoting behavior. As shown in FIG. 1C, the flexurally rigid sleeve 34 can be arranged on the outer circumference of the flexurally rigid shaft.

The construction of the shaver 20 according to the invention will be explained in greater detail on the basis of the detailed drawings in FIGS. 2A-2C.

Figure 2:
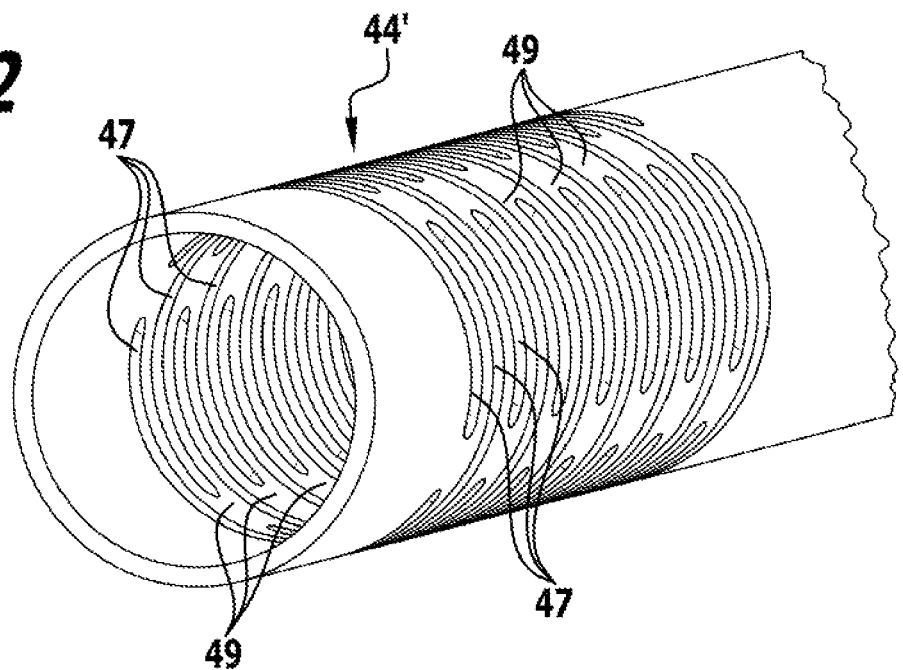
FIGS. 2A, B and C show an outer shaft, a control element as well as an inner shaft of the instrument according to the invention in accordance with FIG. 1B.
FIG. 2D shows an alternative embodiment of the control element of FIG. 2B.
FIGS. 2E and F show two alternative embodiments of sections of articulation for the outer shaft of FIG. 2A.
Figure 2:
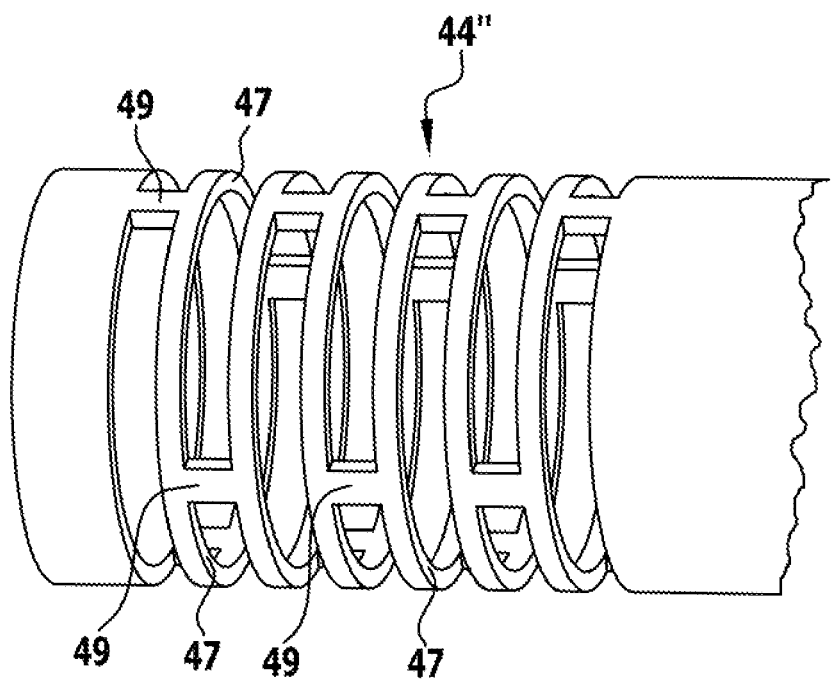

FIG. 2A shows an outer hollow cylindrical shaft 40 with a proximal end area 42, a proximal flexible section 44 adjoining the end area, a flexurally rigid central section 46 adjoining thereon in the direction towards the distal end 52, followed first of all at the distal end section 48 by a flexible section 50, to which a component of a tool 52 is connected or integrally formed. In the present case, the component of the tool is integrally formed on the distal end of the outer shaft 40.

A control element 60 shown in FIG. 2B is inserted into this outer shaft 40 and this control element has a plurality of, in the present case eight, force transferring longitudinal elements 62 which extend parallel to the longitudinal direction of the instrument and are, for example, in the form of cables or wires.

The longitudinal elements 62 are connected to one another in circumferential direction at their proximal and distal ends to form an annular collar 64, 66. The length of the control element 60 extends, as is apparent from a comparison of the illustrations in FIGS. 2A and 2B, from the proximal section of articulation 44 of the outer shaft 40 as far as the distal section of articulation 50 of the outer shaft 40.

FIG. 2D shows an alternative embodiment of a control element 60' which is produced from a one-piece small tube 61, for example, by way of laser beam cutting.

The slits 63 formed in the tube 61 by way of laser beam cutting extend almost over the entire length of the tube 61 and so annular collars 64', 66' which have no slits remain only at the proximal and distal ends and connect the wall segments 65 which function as force transferring longitudinal elements respectively with one another.

An inner shaft 80 is, finally, pushed into the interior of the hollow cylindrical control element 60, as illustrated in FIG. 2C.

The inner shaft 80 also comprises a section of articulation 82 at the proximal end as well as a flexurally rigid central section 84 and a distal section of articulation 86. A tool component 88 is connected to the distal section of articulation 86 and this is arranged in the same position as the tool component 52 of the outer shaft 40 once the inner shaft 80 has been pushed into the outer shaft 40 through the control element 60.

In accordance with one preferred embodiment of the invention, it is provided for the inner shaft 80 to function at the same time as drive element and so the tool components 88 and 52 interact during any rotational movement and, for example, can remove pieces of tissue coming into contact in this area via a cutting, abrasive or milling function.

Since the inner shaft 80 has a free lumen, such pieces of tissue can be conveyed via the lumen of the inner shaft 80 outwards to the proximal end 42 of the instrument and removed.

The configuration of the sections of articulation in the form of the flexible sections 44, 50 and 82, 86 of the inner and outer shafts, respectively, can be manifold.

FIGS. 2E and 2F show two variations of related configurations of the flexible sections, here in the form of the sections 44' and 44'', respectively. The same type of configuration also lends itself to the flexible section 50.

The two variations have in common the use of a slit structure with slits 47 extending in circumferential direction in the hollow cylindrical shaft. Preferably, two or more slits which are separated from one another via webs 49 are present along a circumferential line. Since the arrangement of slits along only one circumferential line would allow only a very small pivoting angle, a plurality of circumferential lines with slits 47, spaced in axial direction, are present in typical slit structures of the area of articulation 44'. Slits 47 arranged adjacent to one another in axial direction are preferably arranged so as to be offset relative to one another in circumferential direction so that bending possibilities result in several planes.

In FIG. 2F, two slits 47, which are separated from one another by webs 49, are present per circumferential line. In FIG. 2E, there are three slits 47. The slit structure typically comprises in both cases a plurality of slits 47 which are arranged along several imaginary circumferential lines which are spaced from one another in axial direction. The admissible pivoting angle may be predetermined very easily via the selection of the slit structure and the number of slits and also additional properties of a section of articulation, such as, for example, bending strength, can be adapted to the respective application.

FIG. 3A shows an alternative control element 90, with which the force transferring longitudinal elements 92 are connected with their proximal and distal ends to proximal and distal annular collars 94, 96, respectively. In contrast to the control element 60, which is shown in FIG. 2B, the force transferring longitudinal elements 92 are not arranged in a straight line and parallel to the longitudinal axis of the control element 90 but rather along helical lines so that the ends of the longitudinal elements 92 end at the annular collars 94, 96 in circumferential direction with an angular offset. The angular offset in circumferential direction is approximately 180° with the embodiment shown in FIG. 3A, with the result that a pivoting movement of the proximal end of the instrument leads to a pivoting movement of the distal end section which runs in the same plane of pivoting but in an opposite direction. Instead of the S shape shown in FIG. 1B, a U shaped, angled instrument configuration is obtained.

Other angular differences are possible, in principle in the full range from 0 to 360°, wherein appreciable advantages will be achieved in the range of approximately 10° to approximately 350°. With an angular offset of 90°, a pivoting movement of the distal end section at right angles to the plane of pivoting of the proximal end section is obtained.

FIG. 3B shows a variation of a control element 90' which is formed from a one-piece small tube by way of laser cutting, similar to the control element 60' of FIG. 2D. The wall segments 92' thereby resulting are separated from one another by slits 93' and are connected to one another in a force locking manner only in the region of annular collars 94', 96'. The advantages of the helical course of the wall segments are the same as those of the control element 90 with the helically extending longitudinal elements 92.

The invention claimed is:

1. Surgical instrument for use in combination with a trocar or the like, comprising:
    a proximal and a distal end section, each end section comprising an area of articulation,
    a flexurally rigid central section arranged between the proximal end section and the distal end section,
    the proximal end section being connectable to an actuating device,
    the distal end section being connectable to a cutting, abrasive or milling tool drivable by means of a drive element,
    an outer hollow cylindrical shaft,
    an inner hollow cylindrical shaft, and
    a control element arranged between the outer shaft and the inner shaft, the control element having two or more force transferring longitudinal elements extending substantially from the proximal to the distal area of articulation of the instrument and transferring at least one of traction and pressure forces,
    wherein:
    the force transferring longitudinal elements are arranged at essentially regular angular distances in a circumferential direction of the instrument and are connected to one another in the circumferential direction at their proximal and distal ends, and
    the force transferring longitudinal elements are guided in a radial direction by the outer shaft and the inner shaft.

2. Instrument as defined in claim 1, wherein the inner shaft is designed as drive element for the cutting, abrasive or milling tool.

3. Instrument as defined in claim 2, wherein the drive element is designed to be essentially torsionally rigid.

4. Instrument as defined in claim 1, wherein at least one of the areas of articulation is designed to be flexurally elastic.

5. Instrument as defined in claim 1, wherein the force transferring longitudinal elements are arranged so as to be laterally spaced relative to one another.

6. Instrument as defined in claim 5, wherein spacer elements are arranged between the force transferring longitudinal elements.

7. Instrument as defined in claim 1, wherein the force transferring longitudinal elements are arranged along a longitudinal direction at least partially in direct contact with one another.

8. Instrument as defined in claim 1, wherein the force transferring longitudinal elements are designed as cables or wires.

9. Instrument as defined in claim 1, wherein the control element comprises a hollow cylindrical component, the cylinder wall of the hollow cylindrical component being subdivided at least in a region of a section between proximal and distal ends of the hollow cylindrical component into two or more wall segments forming the force transferring longitudinal elements.

10. Instrument as defined in claim 9, wherein the two or more wall segments are connected fixedly to one another via an annular collar at the distal end of the hollow cylindrical component.

11. Instrument as defined in claim 9, wherein the two or more wall segments are connected fixedly to one another in a region of the proximal end of the hollow cylindrical component.

12. Instrument as defined in claim 1, wherein at least one of the outer and inner shafts has a flexurally rigid section arranged between the proximal and distal areas of articulation.

13. Instrument as defined in claim 12, wherein the proximal area of articulation has an extension in a longitudinal direction of the instrument differing from an extension of the distal area of articulation.

14. Instrument as defined in claim 13, wherein the extension of at least one of the proximal and distal areas of articulation is adjustable.

15. Instrument as defined in claim 14, further comprising a holding device for fixing in position at least part of at least one of the proximal and distal areas of articulation in a flexurally rigid manner with respect to the longitudinal direction of the instrument or a functional unit adjoining the proximal or distal end section.

16. Instrument as defined in claim 1, wherein:
    at least one of the areas of articulation of the outer and/or inner shaft comprise a wall section,
    several slits spaced from one another and extending in the circumferential direction are arranged in said wall section.

17. Instrument as defined in claim 16, wherein three or more slits are arranged next to one another in an axial direction.

18. Instrument as defined in claim 17, wherein the slits arranged next to one another are arranged so as to be offset relative to one another in the circumferential direction.

19. Instrument as defined in claim 16, wherein the slits are slits penetrating the cylinder wall section completely.

20. Instrument as defined in claim 16, wherein wall surfaces delimiting the slits are arranged at an acute angle in relation to the radial direction.

21. Instrument as defined in claim 20, wherein the wall surfaces of the same slit located opposite one another are arranged in mirror image so that a larger slit width results at an outer circumference of the shaft than adjacent to an inner circumference.

22. Surgical instrument for use in combination with a trocar or the like, comprising:
    a proximal and a distal end section, each end section comprising an area of articulation,
    a flexurally rigid central section arranged between the proximal end section and the distal end section,
    the proximal end section being connectable to an actuating device,
    the distal end section being connectable to a cutting, abrasive or milling tool drivable by means of a drive element,
    an outer hollow cylindrical shaft,
    an inner hollow cylindrical shaft, and a control element arranged between the outer shaft and the inner shaft, the control element having two or more force transferring longitudinal elements extending substantially from the proximal to the distal area of articulation of the instrument and transferring at least one of traction and pressure forces, wherein:

the force transferring longitudinal elements are arranged at essentially regular angular distances in a circumferential direction of the instrument and are connected to one another in the circumferential direction at their proximal and distal ends, and the force transferring longitudinal elements end in different angular positions on the proximal and on the distal end sections when seen in the circumferential direction.

23. Instrument as defined in claim 22, wherein the force transferring longitudinal elements are guided in a radial direction by the outer and the inner shaft.

24. Instrument as defined in claim 22, wherein the force transferring longitudinal elements are arranged in a helical shape at least in sections.

25. Instrument as defined in claim 24, wherein the force transferring longitudinal elements have one or more sections arranged parallel to a longitudinal direction of the instrument.

26. Instrument as defined in claim 22, wherein the force transferring longitudinal elements are arranged in a region of the proximal and/or distal end sections with an essentially parallel alignment in relation to a longitudinal axis of the instrument.

27. Instrument as defined in claim 22, wherein the force transferring longitudinal elements are designed as cables or wires.

28. Instrument as defined in claim 22, wherein at least one of the outer and inner shafts has a flexurally rigid section arranged between the proximal and distal areas of articulation.

29. Instrument as defined in claim 28, wherein the proximal area of articulation has an extension in a longitudinal direction of the instrument differing from an extension of the distal area of articulation.

30. Instrument as defined in claim 29, wherein the extension of at least one of the proximal and distal areas of articulation is adjustable.

* * * * *

UNITED STATES PATENT AND TRADEMARK OFFICE
CERTIFICATE OF CORRECTION

PATENT NO.       : 8,353,898 B2  
APPLICATION NO.  : 13/304803  
DATED            : January 15, 2013  
INVENTOR(S)      : Lutze et al.

Page 1 of 1

It is certified that error appears in the above-identified patent and that said Letters Patent is hereby corrected as shown below:

Column 10, line 46: "slits penetrating the cylinder wall section completely." should read
-- slits penetrating the wall section completely. --

Signed and Sealed this
Nineteenth Day of February, 2013

Teresa Stanek Rea
*Acting Director of the United States Patent and Trademark Office*